United States Patent [19]
Goto et al.

[11] Patent Number: 5,211,637
[45] Date of Patent: May 18, 1993

[54] DEVICE FOR CONNECTING CATHETER AND INJECTION TUBE

[75] Inventors: Yasuhiro Goto; Shin-ichi Hirano, both of Niwa; Kiyoshi Asai, Ashigarakami, all of Japan

[73] Assignees: Kabushiki-Kaisha Tokai-Rika-Denki-Seisakusho, Aichi; Dow Corning Kabushiki-Kaisha, Kanagawa, both of Japan

[21] Appl. No.: 778,081
[22] PCT Filed: Jun. 15, 1990
[86] PCT No.: PCT/JP90/00786
§ 371 Date: Dec. 6, 1991
§ 102(e) Date: Dec. 6, 1991
[87] PCT Pub. No.: WO90/15578
PCT Pub. Date: Dec. 27, 1990
[51] Int. Cl.$^5$ ............................................. A61M 25/00
[52] U.S. Cl. ..................................... 604/283; 128/786; 128/912
[58] Field of Search ....................... 604/103, 283, 905; 606/29, 195; 128/642, 786, 912

[56] References Cited
U.S. PATENT DOCUMENTS
3,568,660  3/1971  Crites et al. ........................... 128/786
4,346,712  8/1982  Handa et al. ........................... 606/195
4,402,319  9/1983  Handa et al. ........................... 606/195

FOREIGN PATENT DOCUMENTS
2578746  9/1986  France ............................... 604/283

Primary Examiner—John D. Yasko
Assistant Examiner—Anthony Gutowski
Attorney, Agent, or Firm—Venable, Baetjer, Howard & Civiletti

[57] ABSTRACT

A device for connecting a catheter to an injection tube, which is provided with an elastic tube into which an open end of the tubular catheter having electrodes disposed at the closed end thereof and also having conductive wires connected to said electrodes and taken out at the open end thereof and an open end of the injection tube having a mechanism for fluid injection at the other end thereof are inserted so that both open ends are connected end-to-end and the conductive wires are taken out through a gap between the elastic tube and the injection tube; and a sealing agent to cover respective surfaces of the catheter, injection tube, and elastic tube which surfaces are coated with an adhesive. The catheter, injection tube, and elastic tube, when coated with an adhesive of high viscosity, are compatible with the hard sealing agent lying thereabove. A casing consisting of half members encloses the sealing agent and the casing increases the strength of the device, whereby the device is prevented from being deformed and prevented from causing leakage of fluid through the gap even when subjected to external force. The device has improved resistance to external pressure. In addition, connection of the conductive wires between the electrodes and the terminals arranged on the side of the casing serves to tightly fix the wires in the sealing agent packed in the case and causes no breakage of the wires, whereby the wires are connected to the external parts through the terminals to thereby provide a device with improved reliability.

1 Claim, 1 Drawing Sheet

PRIOR ART

DEVICE FOR CONNECTING CATHETER AND INJECTION TUBE

TECHNICAL FIELD

This invention relates to device for connecting a catheter having electrodes and an injection tube for injecting a liquid into the catheter.

BACKGROUND ART

A catheter is a hollow tubular instrument which is inserted into the human body from the outside. A catheter may be used to inject a liquid into the body or to extract humor, or it may be is used for maintaining an open state of a passage, and so on.

A catheter having a spherical rubber plug (balloon) attached to its extreme end is popularly used to effect hemostasis (i.e. used to effect the arresting of circulation of blood in a blood vessel which is hemorrhaging). It is inserted into the body to a side of a bleeding internal body portion, for example, a portion of intracerebral hemorrhage which side of the bleeding internal body portion is the side closer to the heart. A thermosetting resin is injected into the spherical rubber plug on the extreme end to expand the plug and to thereby stop flow of blood in the blood vessel. In this case, in order to leave the expanded plug portion on the extreme end of the catheter in the blood vessel which is used to stop the discharge of blood, the expanded plug of the catheter is softened and cut off by heat. The heat is generated by supplying a high-frequency electric current carried by leadwires to electrodes which are located on the end portion of the catheter. In the case of this type of catheter, it is necessary for the catheter to have a cut portion through which leadwires are led out. The leadwires connect the electrodes with a high-frequency current generator. Since the thermosetting resin is injected into the plug of the catheter through an injection tube under pressure, a pressure proof connector is used on the cut portion of the catheter to connect the catheter and the injection tube.

The construction of a prior art connector is as shown in FIG. 2. An elastic tube 5 (silicone tube) is used to connect catheter 1 which has a diameter of 1.2 mm, and is made of Teflon which is poor in adhesion, with injection tube 4 made of the same material. For improvement in bonding strength of the connections, thereby ensuring resistance to a pressure of 15 atm at the maximum instantaneous adhesive 10 having an interfacial effect and having a low viscosity of about 5 to 10 centiPoise is applied to surfaces of the catheter, the injection tube and the elastic tube, and then epoxy adhesive 6 is applied thereon two or three times. Leadwires 3, extending from the electrodes, are led out through a gap between the elastic tube and the injection tube and are connected to the high-frequency current generator by alligator clips.

In this conventional connector, the instantaneous adhesive 10 applied to the surfaces of the catheter, the injection tube and the elastic tube has a low viscosity and is therefore poor in affinity with hard epoxy resin 6 forming the upper layers, and the connector may be deformed if an excessive pressure is applied and if the strength of the epoxy resin is insufficient. There is therefore a risk of formation of a gap and, hence, occurrence of liquid leakage. Thus, the conventional connector entails the problem in terms of being pressure proof. It also entails the problem in terms of reliability owing to the risk of disconnection of the leadwires or the risk of alligator clips coming off since the leadwires are made of fine copper wires having a diameter of 0.05 mm and are connected by the alligator clips.

DISCLOSURE OF THE INVENTION

It is an object of the present invention to provide a device for connecting a catheter with an injection tube which device has pressure proof properties to prevent liquid leaking at the connecting of the catheter with the injection tube and which device helps prevent the leadwires from snapping, thereby to be improved in reliability.

The above-described problems can be solved by providing a device for connecting a catheter and an injection tube comprising (A) an elastic tube into which one opening end of the catheter, the catheter being in the form of a tube, and one opening end of the injection tube, the injection tube having at its other end a mechanism for injecting a liquid, are inserted and butted against each other. The catheter is closed at its other end and has electrodes provided on its closed end and has leadwires connected to the electrodes, the leadwires being led through the one end of the catheter and led out of the elastic tube on the side of the injection tube. The device further comprises (B) a sealing material for covering surfaces of the catheter, the injection tube and the elastic tube which surfaces are coated with an adhesive wherein the adhesive has a high viscosity of about 100 centiPoise, and (C) a casing consisting of half members and having openings through which said catheter and said injection tube extend, and (D) a connection terminal to which said leadwires are connected.

In this construction, the adhesive applied to the surfaces of the catheter, the injection tube and the elastic tube has a high viscosity such as to have good affinity with the hard sealing material forming an upper surface. The casing consisting of half members is provided outside the sealing material. The device is thereby improved in strength and does not deform such as to form a gap and to cause liquid leakage even if an external force is applied; it is improved in pressure proof properties.

Further, the leadwires from the electrodes, which are connected to the connection terminal provided on a side surface of the casing, are fixed in the sealing material filling the casing so as to be prevented from snapping, and are firmly connected to an external unit through the connection terminal, thus improving the reliability of the device.

BEST MODE FOR CARRYING OUT THE INVENTION

Figure 1:
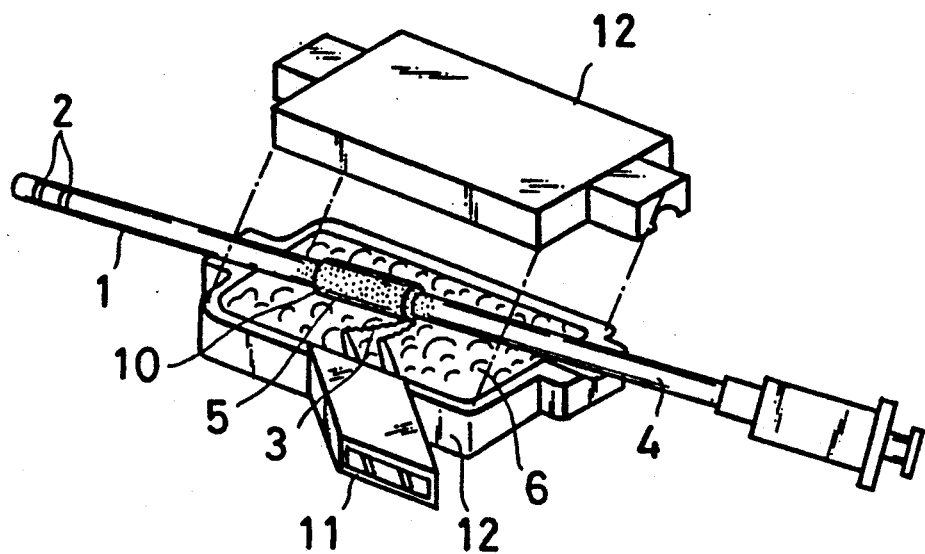
FIG. 1 is a perspective view of a connector which represents an embodiment of the present invention.
Figure 2:
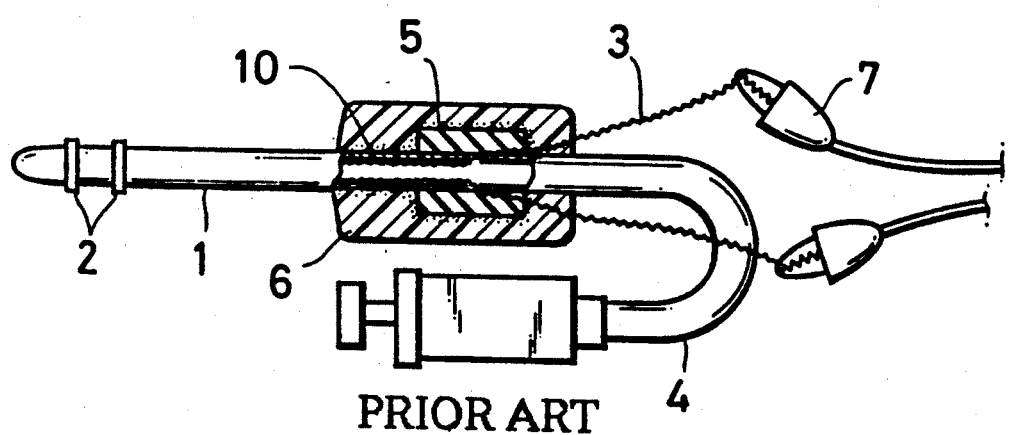
FIG. 2 is a front view of a conventional connector partially in longitudinal section.

The present invention will be described below with reference to FIG. 1 showing the construction of its embodiment in perspective.

Electrodes 2 are provided on an extreme end portion of catheter 1. Leadwires 3 lead from electrodes 2 on the inside of catheter 1 and are led out of catheter 1 at connecting portions of catheter 1 and injection tube 4. The connecting portions of catheter 1 and injection tube 4 are inserted into a rubber tube 5 made of, for example, silicone rubber so tht the opening end surfaces of catheter 1 and injection tube 4 abut against each other. High-viscosity instantaneous adhesive 10 is applied to surfaces of catheter 1, injection tube 4 and rubber tube 5, and the catheter, injection tube and rubber tube are set on one of two half members of a case 12 which said half member has, in its side portions, openings for insertion of the catheter 1 and the injection tube 4, and which has a connection terminal 11 for supplying a high-frequency current through leadwires 3. Leadwires 3 are led out of rubber tube 5 on the side of injection tube 4 and are connected to connection terminals 11. Epoxy adhesive 6 is thereafter filled in said one of the two half members of the case 12, and said half member is bonded to the second half member of the case 12. In the thus-constructed connector, there is no risk of the thermosetting resin leaking through the connecting portion even if the resin is injected through the injection tube 4 at a pressure of about 15 atm, and no risk of the snapping of the leadwires, and no risk of the disconnection of the high-frequency current supplied through the connector 11. The connector is therefore improved in its reliability over the prior art connector.

In accordance with the present invention, the catheter and the injection tube are connected together by an elastic tube and are set on a casing, and the casing is filed with an epoxy resin, thereby improving the strength of the connection and, hence, the pressure proof properties.

Moreover, the leadwires from the electrodes are connected to the connection terminal of the connector provided on a side surface of the casing, and the connection terminals are connected to an external unit, thereby improving the reliability of the connector over the prior art connector.

What is claimed is:

1. A device for connecting a catheter and an injection tube,
   wherein said catheter is a tubular catheter having an open end and electrodes disposed at the closed end thereof and having lead wires connected to said electrodes and taken out at the open end thereof and wherein said injection tube has an open end and has a mechanism for fluid injection at the other end thereof, said device comprising
   (1) an elastic tube into which the open end of said tubular catheter and the open end of said injection tube are inserted so that both open ends are connected end-to-end and said conductive wires are lead out through a gap between the elastic tube and the injection tube;
   (2) a sealing agent to cover respective surfaces of the catheter, injection tube and elastic tube which surfaces are coated with an adhesive wherein said adhesive has a high viscosity and wherein said catheter, injection tube and elastic tube, when coated with said adhesive, are compatible with said sealing agent lying thereabove; and
   (3) a casing comprising half members wherein a connection terminal is arranged on the side of said casing, and wherein said casing has openings through which on one hand said catheter and on the other hand said injection tube extend wherein the ends of said taken out conductive wires connect to said terminal and said casing serves to tightly fix said taken out conductive wires in the sealing agent packed in the case.

* * * * *